_United States Patent_ [19]

Arcamone et al.

[11] 4,125,607

[45] Nov. 14, 1978

[54] DAUNOSAMINYL ANTHRACYCLINONES AND THEIR USE

[75] Inventors: Federico Arcamone; Luigi Bernardi; Pietro Giardino; Aurelio di Marco, all of Milan, Italy

[73] Assignee: Societa' Farmaceutici Italia S.p.A., Milan, Italy

[21] Appl. No.: 737,473

[22] Filed: Nov. 1, 1976

[30] Foreign Application Priority Data

Nov. 18, 1975 [GB] United Kingdom ............... 47559/75

[51] Int. Cl.² .......................................... C07H 15/24
[52] U.S. Cl. ....................................... 424/180; 536/4; 536/17

[58] Field of Search ....................... 536/4, 17; 424/180

[56] References Cited

U.S. PATENT DOCUMENTS

| | | | |
|---|---|---|---|
| 4,020,270 | 4/1977 | Arcamone et al. | 536/4 |
| 4,031,211 | 6/1977 | Patelli et al. | 536/4 |
| 4,039,663 | 8/1977 | Arcamone et al. | 536/18 |

_Primary Examiner_—Johnnie R. Brown
_Attorney, Agent, or Firm_—Hubbell, Cohen, Stiefel & Gross

[57] ABSTRACT

Disclosed is a class of novel daunosaminyl anthracyclinones which are useful in treating Sarcoma 180 ascites.

6 Claims, No Drawings

DAUNOSAMINYL ANTHRACYCLINONES AND THEIR USE

CROSS REFERENCE TO RELATED APPLICATIONS

This application is related to and incorporates by reference the entire contents of copending application Ser. No. 649,825, filed Jan. 16, 1976, now U.S. Pat. No. 4,077,988, which is owned by the unrecorded assignee hereof.

BACKGROUND OF THE INVENTION

This invention relates to daunosaminyl anthracyclinones, having anti-tumor activity.

U.S. Pat. No. 4,077,988 describes and claims anthracyclinones which are related to daunomycinone and which have the general formulae I to IV are described and claimed:

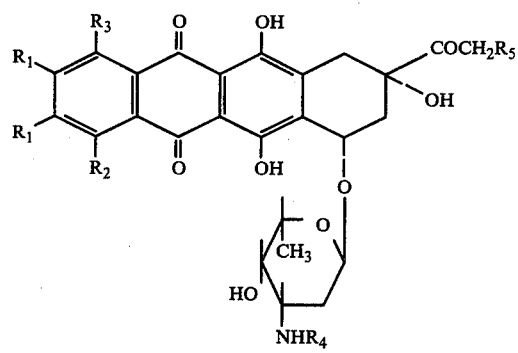

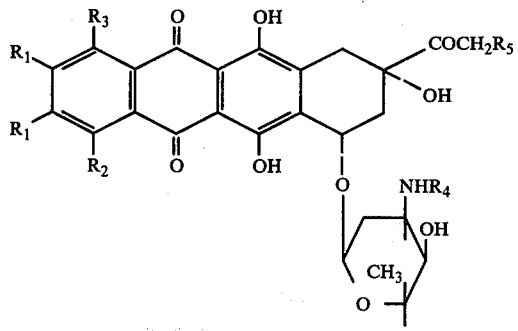

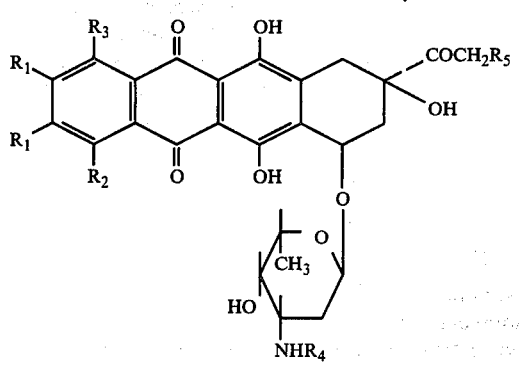

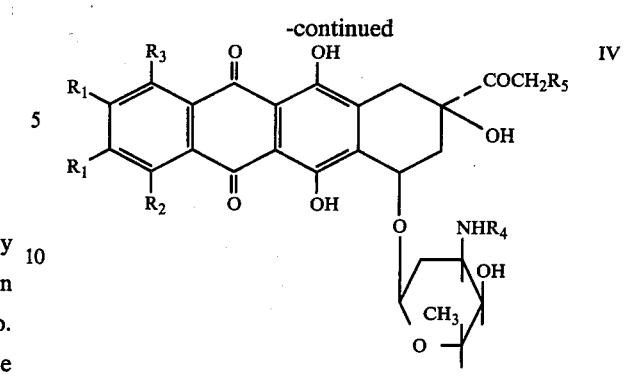

wherein
(a) $R_1$ is hydrogen and $R_2$ and $R_3$ are both hydrogen, methyl, methoxy, chlorine or bromine;
(b) $R_2$ and $R_3$ are both hydrogen and $R_1$ is hydrogen, methyl, methoxy, chlorine or bromine;
(c) $R_4$ is hydrogen or a trifluoroacetyl group; and
(d) $R_5$ is hydrogen.

SUMMARY OF THE INVENTION

In accordance with the present invention, there is provided a new class of compounds of the formulae I to IV

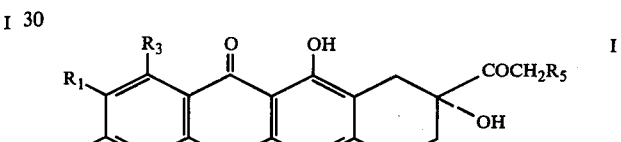

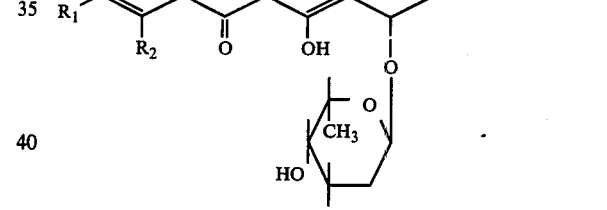

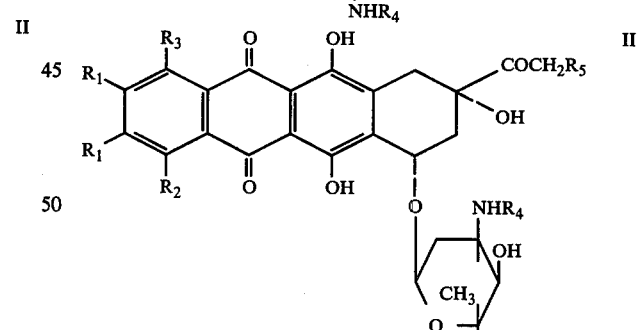

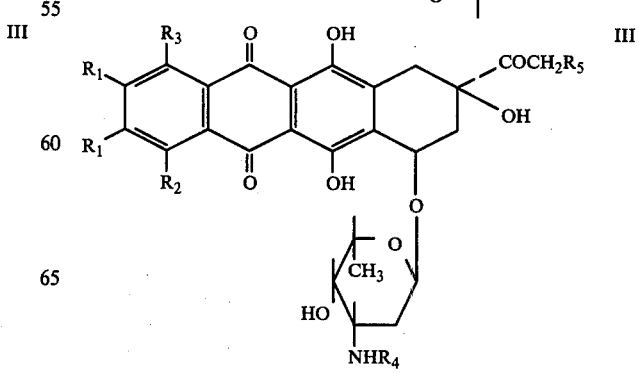

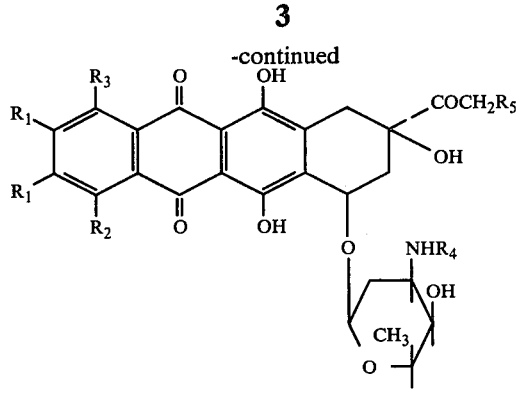

wherein when $R_1$ is hydrogen, $R_2$ and $R_3$ are both hydrogen, methyl, methoxy, chlorine or bromine; when $R_2$ and $R_3$ are both hydrogen, $R_1$ is hydrogen, methyl, methoxy, chlorine or bromine; $R_4$ is hydrogen or trifluoroacetyl; and $R_5$ is OH, $OCOR_6$, $OCOCH_2OCOR_6$, or $NR_7R_8$ wherein $R_6$ is an alkyl having from 6 to 16 carbon atoms, and $R_7$ and $R_8$ are each a lower alkyl group having 1 to 6 carbon atoms or part of a cyclic structure of the formula:

—(CH$_2$)$_4$—; —(CH$_2$)$_5$; —(CH$_2$)$_2$O(CH$_2$)$_2$—; or —(CH$_2$)$_2$—NCH$_3$—(CH$_2$)$_2$—.

These new compounds are related to adriamycin and can be prepared by brominating a compound of the formulae I to IV wherein $R_5$ is hydrogen in accordance with the procedure described in U.S. Pat. No. 3,803,124 to give the corresponding 14-bromo compounds of formulae I to IV ($R_5$=Br). These bromo derivatives are then treated with either sodium formate to make the compounds wherein $R_5$=OH, with the sodium salt of the appropriate carboxylic acid to make the compounds wherein $R_5$=$OCOR_6$, with the sodium salt of the appropriate alkanoylglycolic acid to make the compounds wherein $R_5$=$OCOCH_2OCOR_6$, or with the appropriate amine to make the compounds wherein $R_5$=$NR_7R_8$.

The new compounds of the invention have proven to be distinctly active in the inhibition of malignant or transformed cell growth; in particular they compare quite favorably with the well established anti-cancer drug adriamycin as shown below.

DESCRIPTION OF THE PREFERRED EMBODIMENTS

This invention is illustrated in more detail by the following examples.

EXAMPLE 1

4-demethoxyadriamycin (I, $R_1$=$R_2$=$R_3$=$R_4$=H;$R_5$=OH)

To 1 g (1.87 mM) of 4-demethoxydaunomycin hydrochloride dissolved in 14 ml of methanol and 38 ml of dioxane; 1 ml of ethyl orthoformate was added. The solution was kept at 10° C. and 1.96 mM of bromine in 3 ml of chloroform and 1.17 mM of 2.5 N hydrogen chloride in methanol were added at once. After one hour the solution was poured in a mixture of 100 ml of petroleum ether and 200 ml of diethyl ether. The resulting precipitate was dissolved in 150 ml of dioxane and 150 ml of 0.25 N hydrobromic acid. The solution was kept overnight at 25° C., and a solution of 11 g of sodium formate in 110 ml of water was added. The resulting red solution was kept at 25° C. for 24 hours. The solution was concentrated in vacuo, and the residue was taken up in 200 ml of chloroform/methanol (13/6 by vol.). The solution was washed with 5% aqueous sodium bicarbonate, and then with water. Evaporation of the chloroform left a residue, to which was added one equivalent of hydrogen chloride in diethyl ether to give, after filtration, 0.65 g of 4-demethoxyadriamycin, m.p. 186°–188°.

EXAMPLE 2

4-demethoxy-2,3-dimethyladriamycin (I;$R_2$=$R_3$=$R_4$=H;$R_1$=$CH_3$;$R_5$=OH)

Operating as in Example 1, but employing 1 g of 4-demethoxy-2,3-dimethyldaunomycin (I;$R_2$=$R_3$=$R_4$=$R_5$=H;$R_1$=$CH_3$), 0.55 g of 4-methoxy-2,3-dimethyladriamycin (I;$R_2$=$R_3$=$R_4$=H;$R_1$=$CH_3$;$R_5$=OH) was obtained: m.p. 205°–207° as the hydrochloride.

EXAMPLE 3

4-demethoxy-adriamycin octanoate (I;$R_1$=$R_2$=$R_3$=$R_4$=H;$R_5$=$OCO(CH_2)_6CH_3$)

To 1 g of 4-demethoxydaunomycin hydrochloride dissolved in 14 ml of methanol and 38 ml of dioxane, 1 ml of ethyl orthoformate was added. The solution was kept at +10° C. and 1.96 mM of bromine in 3 ml of chloroform and 1.71 mM of 2.5 N hydrogen chloride in methanol were added at once. After one hour, the solution was poured into a mixture of 100 ml of petroleum ether and 200 ml of diethyl ether. The precipitate was dissolved in 150 ml of dioxane and 150 ml of 0.25 N hydrogen bromide. The solution was kept overnight at 25° C. The solution was repeatedly extracted with chloroform which was discarded, and then with butanol. The butanol extracts were concentrated in vacuo, and on dilution with diethyl ether, 1.1 g of 14-bromo-4-demethoxy-daunomycin (I;$R_1$=$R_2$=$R_3$=$R_4$=H;$R_5$=Br) were collected.

A suspension of this 1.1 g of 14-bromo-4-demethoxy-daunomycin in 500 ml of acetone was treated with 3 g of sodium octanoate at reflux temperature for one hour. Evaporation of the solvent left a residue which was taken up in chloroform. After washing with dilute hydrochloric acid, the solvent was evaporated in vacuo and the residue washed with ethyl acetate and diethyl ether to give 1 g of 4-demethoxy-adriamycin 14-octanoate. IR spectrum: 1730 cm$^{-1}$; 1620 and 1575 cm$^{-1}$ (CO; sharp).

EXAMPLE 4

4-demethoxy-adriamycin 14-hexanoylglycolate (I;$R_1$=$R_2$=$R_3$=$R_4$=H;$R_5$=$OCOCH_2OCO(CH_2)_4CH_3$)

Operating as in Example 3, 14-bromo-4-demethoxydaunomycin was treated with sodium hexanoylglycolate to give 4-demethoxy-adriamycin 14-hexanoylglycolate; Rf 0.32 in a chloroform: methanol: water: 14:6:1 system; I.R. spectrum 1740 cm$^{-1}$ (broad) 1620 and 1575 cm$^{-1}$ (sharp; CO).

EXAMPLE 5

4-demethoxy-14-morpholino-daunomycin (I;$R_1$=$R_2$=$R_3$=$R_4$=H;$R_5$=N-morpholino)

Operating as in Example 3, 14-bromo-4-demethoxy-daunomycin was prepared. Then 1 g thereof was dissolved in 50 ml of t-butanol and 50 ml of chloroform and treated with 3 ml of morpholine. After 3 hours at room temperature the solution was diluted with 500 ml of chloroform and washed repeatedly with water. Evaporation of the solvent left a residue which was taken up in diethyl ether and filtered to give 0.6 g of 4-demethoxy-14-morpholino-daunomycin, electrophoretic mobility=1.73 at pH 1.2 (daunomycin=1).

EXAMPLE 6

4-demethoxy-1,4-dimethyladriamycin
(I;$R_1=R_4=H;R_2=R_3=CH_3;R_5=OH$)

Operating as in Example 1 but employing 1.5 g of 4-demethoxy-1,4-dimethyldaunomycin (I;$R_1=R_4=H;R_2=R_3=CH_3;R_5=H$), 0.62 g of 4-demethoxy-1,4-dimethyladriamycin was obtained.

EXAMPLE 7

4-demethoxy-1,4-dichloroadriamycin
(I;$R_1=R_4=H;R_2=R_3=Cl;R_5=OH$)

Operating as in Example 1 but employing 1 g of 4-demethoxy-1,4-dichlorodaunomycin (I;$R_1=R_4=H;R_2=R_3=Cl;R_5=H$), 0.6 g of 4-demethoxy-1,4-dichloroadriamycin was obtained.

EXAMPLE 8

4-demethoxy-2,3-dichloroadriamycin
(I;$R_2=R_3=R_4=H;R_1=Cl;R_5=OH$)

Operating as in Example 1 but employing 1.1 g of 4-demethoxy-2,3-dichlorodaunomycin (I;$R_2=R_3=R_4=R_5=H;R_1=Cl$), 0.42 g of 4-demethoxy-2,3-dichloroadriamycin was obtained.

BIOLOGICAL ACTIVITY

Biological activity of 4-demethoxyadriamycin in comparison with adriamycin

TABLE 1

Biological activity on cultured HeLa cells. Data are expressed as 50% inhibiting dose (ng/ml) at different times of exposure.

| Compound | $ID_{50}$ 2 hrs. | 8 hrs. | 24 hrs. |
|---|---|---|---|
| 4-demethoxyadriamycin | 1.5 | 0.34 | 0.14 |
| Adriamycin | 125 | 28 | 12.5 |

From the data in Table 1, it can be seen that 4-demethoxy-adriamycin is about one hundred times more active than adriamycin as far as the inhibition of the colony forming ability of HeLa cells "in vitro" is concerned.

TABLE 2

Antitumor activity in mice bearing Sarcoma 180 ascites; single intraperitoneal treatment on day 1. The results are expressed as the time of survival of treated animals as a percentage of the controls (T/C %), the number of long term survivors (LTS) and toxic deaths (TOX).

| Compound | Dose (mg/kg) | T/C % | LTS | TOX |
|---|---|---|---|---|
| 4-demethoxyadriamycin | 0.25 | above 583 | 7/10 | — |
| | 0.5 | above 583 | 6/10 | — |
| | 1.0 | 218 | — | 6/9 |
| Adriamycin | 2.5 | above 583 | 7/10 | — |
| | 5.0 | 211 | 2/10 | 3/9 |
| | 10.0 | 163 | — | 4/10 |

From the data in Table 2, it can be seen that 4-demethoxy-adriamycin is at least ten times more active than adriamycin.

Modifications and variations can, of course, be made without departing from the spirit and scope of our invention.

TABLE 3

| Tumor | Compound | Dose (mg/kg) | T/C % | Tox |
|---|---|---|---|---|
| L 1210 leukemia[1] | Adriamycin | 2.5 | 155 | |
| | | 5 | 166 | 1/10 |
| | | 10 | 155 | 4/10 |
| | 4-demethoxy-adriamycin | 0.25 | 155 | |
| | | 0.5 | 166 | |
| | | 1 | 133 | 10/10 |
| P 388 leukemia[2] | Adriamycin | 2.5 | 173 | |
| | | 5 | 218 | |
| | | 10 | 230 | 1/10 |
| | 4-demethoxy-adriamycin | 0.25 | 168 | |
| | | 0.5 | 195 | |
| | | 1 | 209 | 2/10 |
| Gross leukemia[3] | Adriamycin | 3.5 | 164 | |
| | | 4.4 | 186 | |
| | | 6.0 | 214 | 3/10 |
| | 4-demethoxy-adriamycin | 0.35 | 228 | 1/10 |
| | | 0.45 | 214 | 1/10 |
| | | 0.6 | 157 | 8/10 |

[1]BDF1 mice received $10^5$ ascites cells ip on Day 0 - Treatment ip on Day 1
[2]BDF1 mice received $10^6$ ascites cells ip on Day 0 - Treatment ip on Day 1
[3]C3H/Hc mice received $2\times10^6$ leukemic cells iv on Day 0 - Treatment iv on Days 1, 2, 3.

TABLE 4

Activity on L1210 leukemia
BDF1 mice were injected ip with $10^5$ ascites cells on Day 0 and treated ip on Day 1.

| Compound | Dose (mg/kg) | T/C % | LTS |
|---|---|---|---|
| Adriamycin | 2.9 | 141 | |
| | 4.4 | 152 | 1/10 |
| | 6.6 | 158 | |
| | 10 | 164 | 1/10 |
| 2,3-Dimethyl--4-demethoxy-adriamycin | 1.9 | 152 | |
| | 2.9 | 152 | |
| | 4.4 | 170 | 1/10 |

Having described our invention, what is desired to be secured by Letters Patent and hereby claimed is:

1. A compound of the formulae

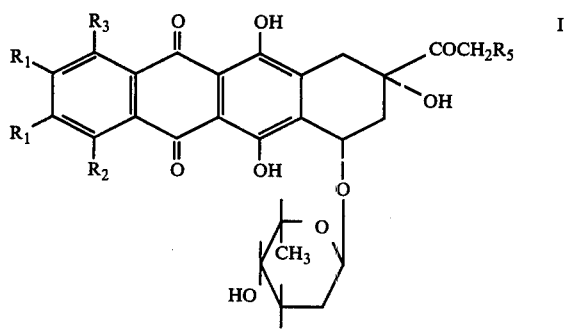

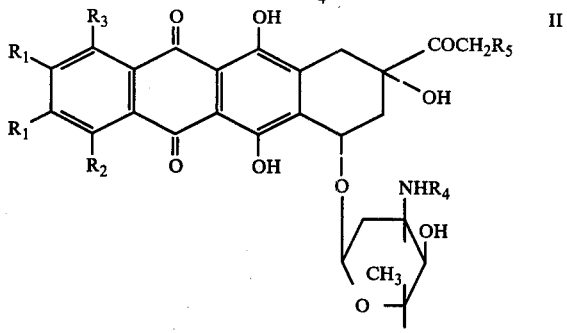

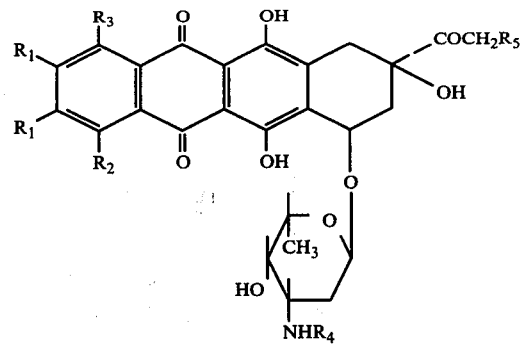

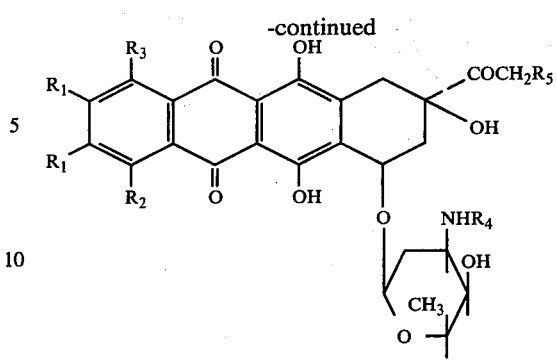

wherein when
R₁ is hydrogen, R₂ and R₃ are both hydrogen, methyl, methoxy, chlorine or bromine; when
R₂ and R₃ are both hydrogen, R₁ is hydrogen, methyl, methoxy, chlorine or bromine;
R₄ is hydrogen or trifluoroacetyl; and
R₅ is OH, OCOR₆, OCOCH₂OCOR₆ or NR₇R₈, wherein R₆ is an alkyl having from 6 to 16 carbon atoms, and R₇ and R₈ are each a lower alkyl group having 1 to 6 carbon atoms or are part of a cyclic structure of the formula: —(CH₂)₄—, —(CH₂)₅—, —(CH₂)₂—O—(CH₂)₂— or —(CH₂)₂—NCH₃—(CH₂)₂— with the proviso that when R₅ is OH, each of R₁, R₂, R₃ and R₄ is hydrogen.

2. A compound according to claim 1 which is 4-demethoxy-adriamycin.

3. A compound according to claim 1 which is 4-demethoxy-adriamycin octanoate.

4. A compound according to claim 1 which is 4-demethoxy-adriamycin-14-hexanoylglycolate.

5. A compound according to claim 1 which is 4-demethoxy-14-morpholino-daunomycin.

6. A method of inhibiting the growth of Sarcoma 180 ascites which comprises administering to a host afflicted therewith, an amount of a compound according to claim 1 sufficient to inhibit the growth thereof.

* * * * *

UNITED STATES PATENT OFFICE
CERTIFICATE OF CORRECTION

Patent No. 4,125,607　　　　　　Dated November 14, 1978

Inventor(s) Federico Arcamone et al

It is certified that error appears in the above-identified patent and that said Letters Patent are hereby corrected as shown below:

Column 1, line 14: "unrecorded assignee" should read -- assignee --.

Signed and Sealed this

Twelfth Day of June 1979

[SEAL]

Attest:

RUTH C. MASON
Attesting Officer

DONALD W. BANNER
Commissioner of Patents and Trademarks